United States Patent [19]

Schirmann et al.

[11] 4,221,675

[45] Sep. 9, 1980

[54] PERCOMPOUND ACTIVATORS

[75] Inventors: Jean-Pierre Schirmann, Oullins; Bernard Dubreux, Francheville-le-Bas; Michel Bakes, La Celle Saint Cloud; Serge Y. Delavarenne, Francheville-le-Haut; Marie-Christine Daude-Lagrave, Paris, all of France

[73] Assignee: Produits Chimiques Ugine Kuhlmann, Paris, France

[21] Appl. No.: 908,781

[22] Filed: May 23, 1978

Related U.S. Application Data

[62] Division of Ser. No. 764,642, Feb. 1, 1977, abandoned.

[30] Foreign Application Priority Data

Feb. 10, 1976 [FR] France ............................... 76 03580

[51] Int. Cl.[2] ........................ C09K 3/00; C07C 69/02; C07C 69/12

[52] U.S. Cl. ............................... 252/186; 260/453 R; 260/453 RZ; 560/250; 560/253; 423/272; 423/273; 252/99

[58] Field of Search .................... 260/453 RZ, 453 R; 560/250, 253; 252/186, 99; 423/272, 273

[56] References Cited

U.S. PATENT DOCUMENTS

| | | | |
|---|---|---|---|
| 2,290,881 | 7/1942 | Katzman | 560/253 |
| 2,477,816 | 8/1949 | Masset | 560/250 |

*Primary Examiner*—John M. Ford
*Assistant Examiner*—Robert C. Whittenbaugh
*Attorney, Agent, or Firm*—Brooks, Haidt, Haffner & Delahunty

[57] ABSTRACT

Percompound activators comprising α-acyloxy-N-acylacetamides having the formula

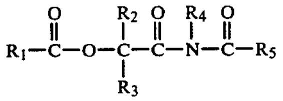

where $R_1$, $R_2$, $R_3$, $R_4$, and $R_5$ are hydrogen or hydrocarbon radicals optionally substituted by other groups, used to activate percompounds in oxidizing and bleaching of textile fibers, oils, fats, and waxes, for cosmetic hair and skin treatment, metal surface passivation, purification, disinfection, and sterilization, the activators providing more rapid action at a given temperature and being useful at lower temperatures.

8 Claims, No Drawings

PERCOMPOUND ACTIVATORS

This application is a division of Ser. No. 764,642, filed Feb. 1, 1977, now abandoned.

BACKGROUND OF THE INVENTION

The present invention relates to novel activators for percompounds, and more particularly, it relates to the use of a α-acyloxy-N-acylamides as activators for inorganic and organic compounds such as aqueous hydrogen peroxide and its addition products with organic substances such as urea and dicyclohexylamine, as well as mineral persalts such as perborate, percarbonates and perphosphates.

The action of aqueous solutions of percompounds used as bleaching and oxidizing agents becomes effective only at temperatures above 70° C., and temperature of from 80° to 100° C. are preferable. The prior art describes a number of products showing properties useful as activators for percompounds. That is, they provide a more rapid oxidizing action or bleaching action than that which is usually observed, or alternatively, they develop this activity under milder temperature conditions than those which are necessary to obtain the activity in their absence. All of these compositions are characterized by the fact that they possess one or more perhydrolyzable functions.

In the area of bleaching, a certain number of activator compounds have been recognized for commercial development. The literature on this subject makes mention chiefly of poly-N hetrocyclic acetyls of the hydantoin, glycoluril, benzimidazole and diketopiperazine types. Nevertheless, this avenue of development has not been followed because these substances present major drawbacks in that they are unstable atmosphere moisture and are spontaneously hydrolyzed, thus rapidly destroying their value as activators.

Moreover, these products necessitate special precautions during storage, handling, and addition to the other ingredients, such as those, for instance, usually incorporated in detergent powders. Various solutions have been proposed to alleviate these deficiencies. Among these are coating, separate packaging, or addition of dessicants. Unfortunately, none of these methods is satisfactory. They pose technical difficulties in practical usage, and they considerably increase the cost of manufacture of the active material.

It can thus be appreciated that there is a considerable commercial need to provide percompond activators which will be stable over a period of time in the solid state under normal packaging and storage conditions.

THE INVENTION

Briefly, the present invention relates to stable α-acyloxy-N-acylamide activators for percompounds. The α-acyloxy-N-acylamides correspond to the formula

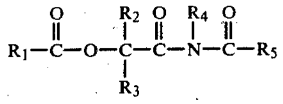

wherein $R_1$, $R_4$, and $R_5$ are the same or different and are hydrogen, straignt-chain alkyl radicals having one to 11 carbon atoms, branched alkyl and cycloalkyl radicals having three to 12 carbon atoms, or hydrocarbon radicals having six to 12 carbon atoms and comprising at least one benzene ring, and $R_2$ and $R_3$ are the same or different and are hydrogen, straight-chain alkyl radical: having one to 11 carbon atoms, branched alkyl and cycloalkyl radical: having three to 12 carbon atoms, hydrocarbon radicals having six to 12 carbon atoms and comprising at least one benzene ring, or straight- and branched-chain alkylene radicals having from two to 11 carbon atoms.

The foregoing radicals can in certain embodiments optionally be substituted with other functional groups. By way of illustation, preferred groups include hydroxy, chloro, bromo, fluoro, iodo, nitro, alkoxy, amino, carbonyl, nitrile, ester, amide, ether, and the like.

Examples of α-acyloxy-N-acylamides which are particualrly useful as percompound activators in certain embodiments of this invention include 2-acetoxy-N-acetylacetamide, 2-acetoxy-N-acetylpropionamaide, 2-acetoxy-N-acetylbutyramide, 2-acetoxy-N-acetylisobutyramide, 2-acetoxy-2-methyl-N-acetylbutyramide, 2-acetoxy-2-isobutyl-N-acetylpropionamide, 1-acetoxy-N-acetylcyclohexane carboxamide, and the like.

It will be understood from the present disclosure that the quantity of acylamide activator can be varied according to the particular requirements of the persalt and its field of use. Thus, the quantity of acylamide activator used can be lesser or greater than the molar quantity of percompound being activated. It has generally been found desirable to have a molar amount of activator in the ratio of from about 0.1 to about ten, based on the percompound to be activated. In certain preferred embodiments, about 0.33 mole of acylamide activator is used for each mole of percompound.

The activators of the invention can be used in all cases where a percompond provides oxidizing or bleaching activity. Thus, the activators of the present invention can be used with the percompounds in bleaching textile fibers, oils, fats, or waxes, for the cosmetic treatment of hair or skin, for passivating metal surfaces, and for purification, disinfection, and sterilization procedures.

The peroxygen compounds which are activated by the acylamide materials include hydrogen peroxide and its addition compounds, and the present invention is especially useful for organic percompounds such as the addition products of hydrogen peroxide with urea, dicyclohexylamine and the like, and inorganic percompounds such as perborates, percarbonates, perphosphates and the like. Alkaline earth metal and alkali metal inorganic persalts are useful, and alkali metal salts, such as those of sodium and potassium, are particularly preferred.

The acylamide activators of the present invention can be added to the percompounds themselves or to a formulation which contains one or more percompounds. Thus, the activators of this invention can be added to a powdered detergent so that a bleaching or oxidizing effect can be more rapidly obtained at a given temperature. The activators can equally well be used to obtain the same bleaching effect at a lower temperature.

Thus, in the presence of sodium perborate in a detergent environment, the acylamide activators of the present invention provide a bleaching action at temperature of from 30° to 50° C. which is substantially equivalent to that obtained at elevated temperatures of the order of 80° C. without the activator(s).

The following examples are given to illustrate embodiments of the invention as it is presently preferred to practice it. It will be understood that these examples are illustrative, and the invention is not to be considered as restricted thereto except as indicated in the appended claims.

EXAMPLE I

A compartment of an AHIBA (G VI B) water bath maintained at 40° C. is charged with 250 ml of an aqueous solution containing 5 g per liter of washing powder having the following composition:

| Component | Weight Percent |
| --- | --- |
| Sodium silicate, $Na_2SiO_2$ | 5.34 |
| Sodium sulfate, $Na_2SO_4$ | 7.25 |
| Sodium carbonate, $Na_2CO_3$ | 2.65 |
| Disodium phosphate, $Na_2HPO_4$ | 0.96 |
| Sodium pyrophosphate, $Na_4P_2O_7$ | 3.99 |
| Sodium tripolyphosphate, $Na_5P_3O_{10}$ | 30.41 |
| Sodium metaphosphate, $NaPO_3$ | 11.92 |
| Water | 18.9 |
| Surfactants | 14. |
| miscellaneous balance to | 100.00 |

and 1.7 gram per liter of sodium perborate tetrahydrate. Another compartment of the vessel is charged with the same solution additionally containing 2-acetoxy-N-acetylacetamide at a concentration of one gram per liter. Into each of these compartments is placed a piece of "Empa" cotton cloth soiled with wine stains standardized by the St. Gall, Switzerland, laboratory.

After 15 minutes of washing at 40° C., the test cloths are rinsed in a stream of cold water and dried at room temperature.

The bleaching power is defined as the difference between the whiteness indices (measured through the use of a Carl Zeiss "Elrepho" spectrophotometer, with a No. 6 filter) before and after washing, reported in percentage with a maximum white of 100. The formula used is $$\text{Percent whitening} = \frac{\text{Change in whiteness}}{100 - \text{Initial whiteness}} + 100$$

Based upon this criterion the foregoing treatment shows a 40.7% whitening without activator, and 58.1% with activator.

EXAMPLES II-XIV

Tests are repeated under the same conditions as Example I varying the type of stains, the temperature, and the activator. The results of these tests are given in Table I:

TABLE I

| Example | Type Of Stain | Washing Temperature | Activator | Concentration | Percent Whitening Without Activator | With Activator |
| --- | --- | --- | --- | --- | --- | --- |
| II | Wine | 40° C. | 2-Acetoxy- | 0.5 g/l | 39.9 | 56.1 |
| III | Wine | 40° C. | 2-Acetoxy-N-acetylacetamide | 2 g/l | 39.7 | 62. |
| IV | Wine | 40 | 2-Acetoxy-N-acetylpropionamide | 39.9 | 57. | |
| V | Wine | 40 | 2-Acetoxy-N-acetylisobutyramide | 1 | 39.9 | 57 |
| VI | Wine | 30 | 2-Acetoxy-N-acetylacetamide | 1 | 38.1 | 54 |
| VII | Wine | 30 | 2-Acetoxy-N-acetylpropionamide | 1 | 38.1 | 49 |
| VII | Wine | 20 | 2-Acetoxy-N-acetylacetamide | 1 | 31.7 | 45 |
| IX | Wine | 20 | 2-Acetoxy-N-acetylpropionamide | 1 | 31.7 | 41 |
| X | Tea | 20 | 2-Acetoxy-N-acetylacetamide | 1 | 44 | 56 |
| XI | Tea | 40 | 2-Acetoxy-N-acetylacetamide | 0.5 | 44.4 | 53 |
| XII | Tea | 40 | 2-Acetoxy-N-acetylacetamide | 2 | 44.4 | 63 |
| XIII | Tea | 40 | 2-Acetoxy-N-acetylpropionamide | 1.08 | 45.3 | 54 |
| XIV | Tea | 40 | 2-Acetoxy-N-acetylisobutyramide | 1.17 | 45.3 | 52 |

Certain of the α-acylozy-N-acylacetamides are new compounds which are prepared by reacting the appropriate anhydride or anhydrides with the appropriate cyanohydrin at temperatures of from about 0° to about 50° C. in the presence of an acid catalyst, such as a mineral acid, a strong peracid or aromatic sulfonic acid, or a Lewis acid such as aluminum chloride, boron trifluoride, and the like. Thus, 0.5 ml glycolonitrile and one mole acetic anhydride react in the presence of one gram of sulfuric acid to produce 2-acetoxy-N-acetylacetamide:

What is claimed is:

1. Activated compositions comprising a percompound and at least one α-acyloxy-N-acetylacylamide activator which is 2-acetoxy-N-acetylacetamide, 2-acetoxy-N-acetylpropionamide, 2-acetoxy-N-acetylbutyramide, 2-acetoxy-N-acetylisobutyramide, 2-acetoxy-2-methyl-N-acetylburyramide, 2-acetoxy-2-isobutyl-N-acetylpropionamide, or 1-acetoxy-N-acetylcyclohexane carboxamide.

2. An activated composition according to claim 1 wherein the oxidizer is hydrogen peroxide or its addition compounds.

3. An activated composition according to claim 1 wherein the oxidizer is a percompound which is a perborate, a percarbonate, or a perphosphate.

4. An activated composition according to claim 1 wherein the molar ratio of activator to oxidizer is from 0.1 to ten.

5. An activated composition according to claim 1 wherein the molar ratio of activator to percompound oxidizer is about 0.33.

6. A detergent composition containing an activator according to claim 1.

7. A method for activating percompounds which comprise incorporating with the percompound a small quantity of at least one activator according to claim 1 effective to improve the activ of the percompound.

8. A composition according to claim 1 wherein the activator is 2-acetoxy-N-acetylacetamide, 2-acetoxy-N-acetylpropionamide, 2-acetoxy-N-acetylbutyramide, 2-acetoxy-N-acetylisobutyramide, 2-acetoxy-2-methyl-N-acetylbutyramide, 2-acetoxy-2-isobutyl-N-acetylpropionamide, or 1-acetoxy-N-acetylcyclohexane carboxamide.

* * * * *

UNITED STATES PATENT AND TRADEMARK OFFICE

CERTIFICATE OF CORRECTION

PATENT NO. : 4,221,675

DATED : September 9, 1980

INVENTOR(S) : JEAN-PIERRE SCHIRMANN et al

It is certified that error appears in the above-identified patent and that said Letters Patent are hereby corrected as shown below:

Column 1, line 10, delete "a"; line 18, change "temperature" to --temperatures--; line 32, correct spelling of "heterocyclic"; line 36, after "unstable" delete "atmosphere" and insert --to atmospheric--; line 50, correct spelling of "percompound"; line 66, correct spelling of "straight". Column 2, lines 3 and 5, change "radical" to --radicals--; lines 15-16, correct spelling of "particularly"; line 18, correct spelling of "acetylpropionamide"; line 37, correct spelling of "percompounds". Column 4, Table I, Example IV, under "Concentration" change "39.9" to --1--; under "Without Activator" change "57." to --39.9--, and under "With Activator" insert --57.3--; Table I, last column, change "49" in Example VII to --49.9--; "45" in Example VII to --45.2--; "41" in Example IX to --41.1--; "56" in Example X to --56.2--; "53" in Example XI to --53.2--; "63" in Example XII to --63.4--; "54" in Example XIII to --54.4--, and "52" in Example XIV to --52.5--; line 60, correct spelling of "acyloxy". Column 5, line 10, correct spelling of "acetylbutyramide". Column 6, line 10, change "comprise" to --comprises--; line 12, change "activ" to --activity--.

Signed and Sealed this

*Twenty-fourth* Day of *February 1981*

[SEAL]

*Attest:*

RENE D. TEGTMEYER

*Attesting Officer*

*Acting Commissioner of Patents and Trademarks*